US00PP26790P3

(12) United States Plant Patent
Meilland et al.

(10) Patent No.: US PP26,790 P3
(45) Date of Patent: Jun. 7, 2016

(54) LANDSCAPE SHRUB ROSE PLANT NAMED 'MEIRADENA'

(50) Latin Name: *Rosa hybrida*
Varietal Denomination: Meiradena

(71) Applicant: CP DELAWARE, INC., Wilmington, DE (US)

(72) Inventors: Alain A. Meilland, Antibes (FR); William J. Radler, Greenfield, WI (US)

(73) Assignee: CP DELAWARE, INC., Wilmington, DE (US)

( * ) Notice: Subject to any disclaimer, the term of this patent is extended or adjusted under 35 U.S.C. 154(b) by 111 days.

(21) Appl. No.: 14/120,808

(22) Filed: Jul. 1, 2014

(65) Prior Publication Data

US 2016/0007516 P1 Jan. 7, 2016

(51) Int. Cl.
*A01H 5/02* (2006.01)

(52) U.S. Cl.
USPC ..... Plt./103

(58) Field of Classification Search
USPC ..... Plt./103
See application file for complete search history.

*Primary Examiner* — Anne Grunberg
(74) *Attorney, Agent, or Firm* — Buchanan Ingersoll & Rooney PC

(57) ABSTRACT

A new and distinct Landscape Shrub rose plant is provided that abundantly and substantially continuously forms attractive cup-shaped double white blossoms. The plant exhibits vigorous vegetation and a compact and bushy growth habit. The foliage is attractive dark green and contrasts well with the blossom coloration. The disease resistance has been found to be excellent during observations to date. The plant is well suited for providing attractive ornamentation in in the landscape.

2 Drawing Sheets

Botanical/commercial classification: *Rosa hybrida*/Landscape Shrub Rose Plant.

Varietal denomination: cv. Meiradena.

SUMMARY OF THE INVENTION

The new variety of *Rosa hybrida* Landscape Shrub rose plant was created at Le Luc en Provence, France, by artificial pollination during June 2007 wherein two parents were crossed which previously had been studied in the hope that they would contribute the desired characteristics. The female parent (i.e., the seed parent) was an unnamed and unreleased breeder seedling (non-patent in the United States). The male parent (i.e., the pollen parent) was the 'Radsweet' variety (U.S. Plant Pat. No. 19,032).

The parentage of the new variety can be summarized as follows:

Unnamed Breeder Seedling×'Radsweet'.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly and substantially continuously forms attractive cup-shaped double white blossoms,
(b) exhibits a compact and bushy growth habit,
(c) forms vigorous vegetation,
(d) forms attractive dense dark green foliage that contrasts well with the blossom coloration,
(e) exhibits excellent disease resistance, and (f) is well suited for growing as attractive ornamentation in the landscape.

The new variety well meets the needs of the horticultural industry. It can be grown to advantage as ornamentation in parks and gardens, public areas, and residential landscapes. Accordingly, the plant is particularly well suited for growing in the landscape.

The new variety can be readily distinguished from other landscape shrub rose plants through an inspection of the blossoms. For instance, the 'Radsweet' male parent forms dissimilar single blossoms having a light pink coloration. When compared to the 'Radwhite' variety, it is found that the 'Radwhite' variety (U.S. Plant Pat. No. 20,273) forms dissimilar single blossoms.

The rooting of terminal cuttings was used to asexually propagate the new cultivar in Le Luc, France, where the initial seedling was germinated. Replicates of the rooted terminal cuttings were also sent to West Grove, Pa., U.S.A., where they were grown. Further asexual reproduction (by way of rooted cuttings) was initiated in West Grove, Pa., U.S.A., and the seedlings were then sent to and grown in Wasco, Calif., U.S.A. From all of these asexual reproductions, the characteristics of the new variety were found to be homogeneous and stable and to be strictly transmissible by asexual propagation. The new variety reproduces in a true-to-type manner by such asexual propagation, such as budding, grafting, and the rooting of cuttings.

The new variety has been named 'Meiradena', and is being marketed under the ICECAP trademark.

BRIEF DESCRIPTION OF THE PHOTOGRAPHS

The accompanying photographs show, as nearly true as it is reasonably possible to make the same in color illustrations of this character, typical flowering rose plants of the new variety.

The illustrated rose plants of the new variety were approximately two years of age and were observed during May 2011, while growing outdoors on their own roots at Le Luc en Provence, France.

DETAILED BOTANICAL DESCRIPTION

Figure 1:
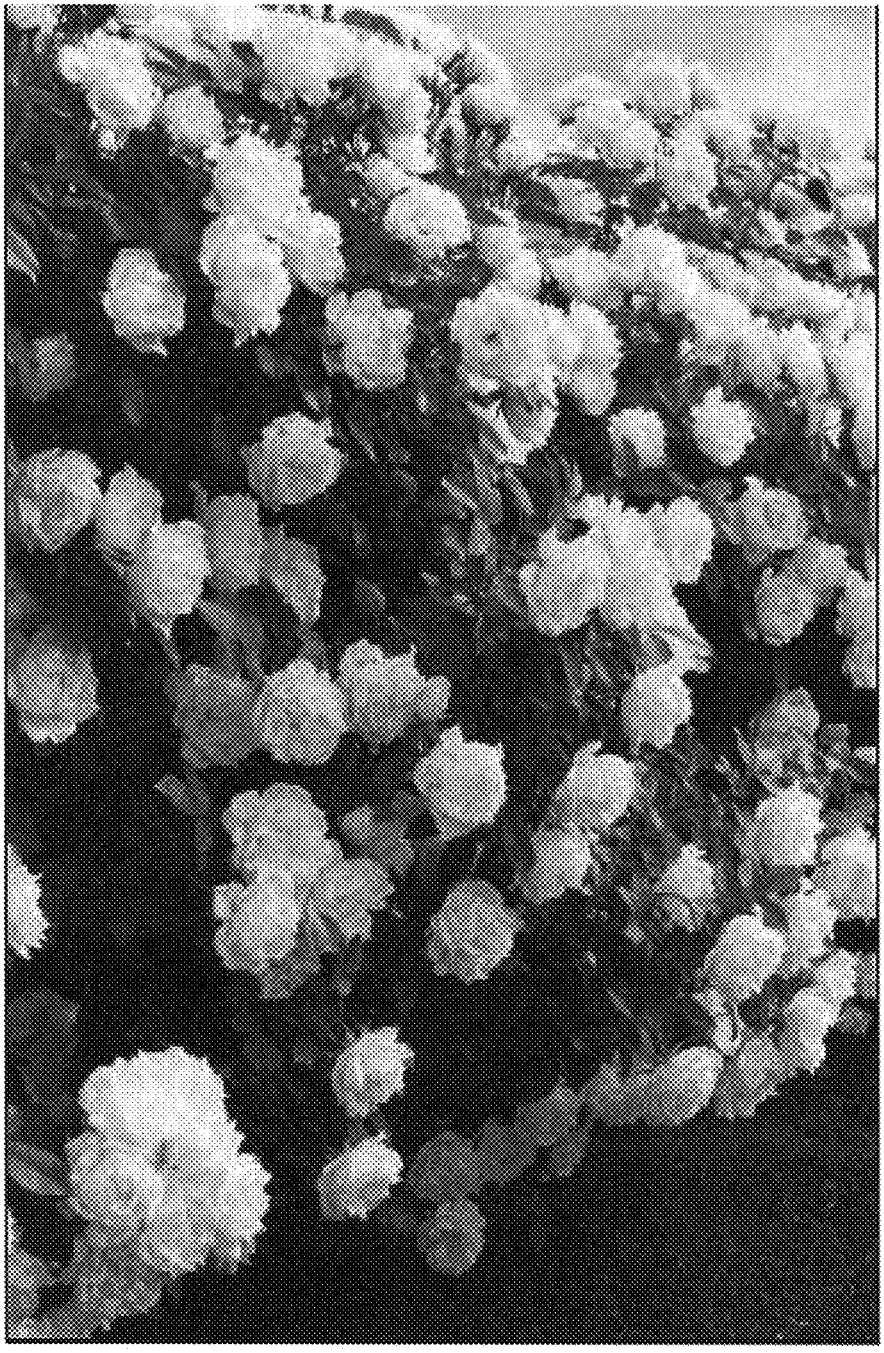
FIG. 1 illustrates the abundant flowering of new plant with the white blossoms contrasting nicely with the dark green foliage.
Figure 2:
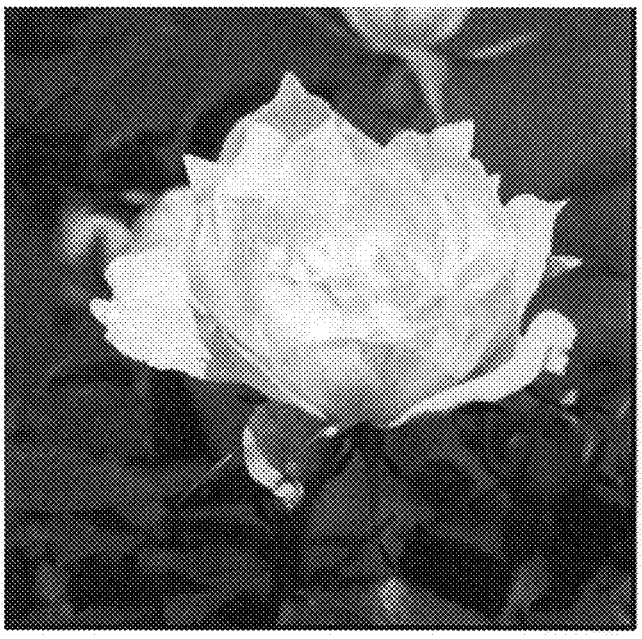
FIG. 2 illustrates a closer view of an open white cup-shaped blossom of the new plant with surrounding foliage.

The chart used in the identification of colors is that of The Royal Horticultural Society (R.H.S. Colour Chart—1995 Edition or equivalent), London, England. The description is based on the observation of two-year-old specimens of the new variety during May while growing in containers outdoors on their own roots at West Grove, Pa., U.S.A.

Class: Landscape Shrub Rose.

*Cultivar*.—Meiradena.

Plant:

*Height*.—Approximately 80 cm on average at maturity.

*Width*.—Approximately 105 cm on average at maturity.

*Habit*.—Compact and bushy.

Branches:

*Color*.—A near Green Group 137C on young stems, and commonly near Greyed-Orange Group 165A on mature wood.

*Length*.—Commonly approximately 19 cm on average for main stems, and approximately 28 cm on average for secondary stems.

*Thorns*.—Size: on young stems commonly approximately 1 cm in length on average, and approximately 5 mm in width on average at the point of attachment, and on adult stems approximately 9 mm in length on average, and approximately 5 mm in width on average at the point of attachment. Color: commonly near Yellow-Green Group 144C on young stems, and near Greyed-Brown Group 199D when mature.

Leaves:

*Size*.—Commonly approximately 11.5 cm in length on average and approximately 9.5 cm in width on average for a five-leaflet leaf.

*Leaflets*.—Number: 3, 5, and 7. Length: approximately 4.5 cm on average for a terminal leaflet, and approximately 3.5 cm for a lower leaflet. Width: approximately 3 cm on average for a terminal leaflet, and approximately 2.5 cm for a lower leaflet. Shape: generally ovate. Apex: acuminate. Base: rounded. Texture: generally glabrous on the upper surface and generally smooth on the under surface. Overall appearance: attractive dark green leaves. Color: (when young): Upper surface: near Green Group 143A. Under surface: near Green Group 138A. Color (when fully mature): Upper surface: near Green Group 137A. Under surface: near Green Group 137A.

Inflorescence:

*Number of flowers*.—Commonly 10 to 20 blooms per stem or in cluster, and commonly approximately 85 blooms per plant on average.

*Peduncle*.—Commonly Yellow-Green Group 144A in coloration, smooth in texture, commonly approximately 5.5 cm in length on average, and approximately 2 mm in diameter on average

*Sepals*.—Number: 5. Margins: entire commonly with extensions on two or three sepals that measure approximately 6 mm in length on average and approximately 1 mm in width on average. Color: on upper surface smooth, near Yellow-Green Group 144B, and covered with short pubescence, and on the under surface smooth, and near Yellow-Green Group 144A.

*Buds*.—Shape: generally ovoid. Length: approximately 3 mm on average as the calyx breaks. diameter: approximately 1.5 cm on average as the calyx breaks. Color: near Yellow-White Group 159C blending to Green-White Group 157B at the base.

*Flower*.—Form: double, cuplike. Diameter: commonly approximately 5.5 cm on average. Color (when opening begins): Upper surface: near Yellow Group 10D at the point of attachment, transitioning to Yellow-White Group 158C towards the apex. Under surface: near Yellow Group 11D at the point of attachment blending to White Group 155D towards the apex. Color (at the end of blooming): Upper surface: near White Group 155D at the point of attachment, blending to White Group 155D towards the apex. Under surface: near Green-Winter Group 157D at the point of attachment blending to White Group 155B towards the apex. Fragrance: none noticeable. Petal number: commonly approximately 25 on average under normal growing conditions. Petal arrangement: imbricated. Petal length: commonly approximately 3.8 cm on average. Petal width: commonly approximately 3.5 cm on average. Petal shape: obcordate. Petal margin: wavy. Petal base: rounded. Petal drop: good, the petals commonly detach cleanly and freely drop upon full maturity. Stamen number approximately 60 on average. Anthers: near Greyed-Orange Group 165D in coloration. Filaments: approximately 1 cm in length, and the coloration is near Yellow Group 4B. Pollen: moderate in quantity, and commonly near Orange Group 26B in coloration. Pistils: approximately 45 on average, generally separate and free. Styles: commonly 5 mm in length, the upper portion commonly is near Red-Purple Group 58D in coloration, and the lower portion commonly is near White Group 155D in coloration. Stigma: commonly approximately 1 mm in diameter on average, and near Yellow Group 11D in coloration. Receptacle: commonly substantially round in shape, approximately 6 mm in diameter average, smooth in texture, achenes stand on the bottom and wall, and near Yellow-Green Group 144A in coloration. Hips/seeds: none observed to date.

Development:

*Vegetation*.—Vigorous and strong.

*Blossoming*.—Abundant and substantially continuous from spring to first frost.

*Resistance to diseases*.—Excellent for the type during observations to date.

Plants of the 'Meiradena' variety have not been observed under all possible environmental conditions to date. Accordingly, it is possible that the phenotypic expression may vary somewhat with changes in light intensity and duration, cultural practices, and other environmental conditions.

We claim:

1. A new and distinct Landscape Shrub rose plant characterized by the following combination of characteristics:

(a) abundantly and substantially continuously forms attractive cup-shaped double white blossoms,
(b) exhibits a compact and bushy growth habit,
(c) forms vigorous vegetation,
(d) forms attractive dense dark green foliage that contrasts well with the blossom coloration,
(e) exhibits excellent disease resistance, and
(f) is well suited for growing as attractive ornamentation in the landscape;

substantially as herein shown and described.

* * * * *